United States Patent
Rumpf et al.

(10) Patent No.: US 7,342,139 B2
(45) Date of Patent: Mar. 11, 2008

(54) METHOD FOR PRODUCING HIGHLY CONCENTRATED FORMALDEHYDE SOLUTION

(75) Inventors: Bernd Rumpf, Hockenheim (DE); Eckhard Ströfer, Mannheim (DE); Ortmund Lang, Quirnbach (DE); Neven Lang, Mannheim (DE)

(73) Assignee: BASF Aktiengesellschaft (DE)

( * ) Notice: Subject to any disclaimer, the term of this patent is extended or adjusted under 35 U.S.C. 154(b) by 39 days.

(21) Appl. No.: 10/588,662

(22) PCT Filed: Feb. 10, 2005

(86) PCT No.: PCT/EP2005/001318

§ 371 (c)(1), (2), (4) Date: Aug. 7, 2006

(87) PCT Pub. No.: WO2005/077877

PCT Pub. Date: Aug. 25, 2005

(65) Prior Publication Data

US 2007/0135660 A1   Jun. 14, 2007

(30) Foreign Application Priority Data

Feb. 11, 2004   (DE) ............... 10 2004 006 649

(51) Int. Cl.
*C07C 45/78* (2006.01)

(52) U.S. Cl. .................... 568/492; 568/493
(58) Field of Classification Search .......... None
See application file for complete search history.

(56) References Cited

U.S. PATENT DOCUMENTS

2005/0040359 A1   2/2005   Ströfer et al.

FOREIGN PATENT DOCUMENTS

DE   102 38 248   3/2004
WO   WO-03/040075   3/2003

OTHER PUBLICATIONS

Ullmann's Encyclopedia of Industrial Chemistry, Sixth Edition, 2000 Electronic Release.
Dad Mehrphasenwendelrohr als Hochleistungsstoffaustauscher by Clemens Casper and Jurgen Weinschenck.

*Primary Examiner*—Sikarl A. Witherspoon

(57) ABSTRACT

A process for preparing a high-concentration formaldehyde solution by removing water from a lower-concentration formaldehyde solution having a formaldehyde content of from 5 to 50% by weight, in which the lower-concentration formaldehyde solution is fed to a preheater and heated in the preheater, depressurized via a pressure maintenance device and concentrated in a helical tube evaporator to give a vapor stream and the high-concentration formaldehyde solution as bottom stream, wherein the heated lower-concentration formaldehyde hyde solution is depressurized in the pressure maintenance device to give a two-phase mixture which is fed into the helical tube evaporator, is proposed.

16 Claims, No Drawings

METHOD FOR PRODUCING HIGHLY CONCENTRATED FORMALDEHYDE SOLUTION

RELATED APPLICATIONS

This application is a national stage application (under 35 U.S.C. 371) of PCT/EP2005/001318 filed Feb. 10, 2005, which claims benefit to German application 10 2004 006 649.3 filed Feb. 11, 2004.

The invention relates to a process for preparing a high-concentration formaldehyde solution by removing water from a formaldehyde solution having a lower concentration.

Formaldehyde is an important industrial chemical and is used for producing numerous industrial products and consumer articles. Formaldehyde is at present used in over 50 branches of industry, mostly in the form of aqueous solutions or formaldehyde containing synthetic resins. Commercially available, aqueous formaldehyde solutions have total concentrations of from 20 to 55% by weight formaldehyde in the form of monomeric formaldehyde, methylene glycol and polyoxymethylene glycols. Thus, a large amount of water is introduced together with the formaldehyde in syntheses which are employed in industry and proceed with the use of aqueous formaldehyde solutions. This water is generally not necessary in the synthesis. This high water burden determines the size of the reactors, their periphery and also the work-up of the products. Furthermore, the excess water has to be treated and disposed of as wastewater. It may be necessary to separate off the water thermally with a considerable input of energy. It is thus desirable to reduce the water burden in syntheses which require the use of aqueous formaldehyde solutions by using aqueous formaldehyde solutions having the highest possible concentration.

However, the preparation and use of such high-concentration aqueous formaldehyde solutions is problematic since solids precipitate from relatively highly concentrated solutions, in particular at low temperatures. Aqueous formaldehyde solutions containing more than 30% by weight of formaldehyde become turbid even on storage at room temperature, since higher polyoxymethylene glycols (HO(CH$_2$O)$_n$H; n≧8) are formed and precipitate. (Ullmann's Encyclopedia of Industrial Chemistry, Edition, 2000 electronic release, Formaldehyde; chapter 2 (physical properties), 2.2 (aqueous solutions), page 2, third paragraph). Although the solubility of the products present in the aqueous formaldehyde solution increases at higher temperatures, undesirable formation of formic acid by the Cannizzaro reaction occurs. For this reason, high-concentration formaldehyde solutions produced, for example, by distillation at elevated temperatures and pressures have high formic acid contents and thus low pH values.

In DE-A 102 38 248, it is stated that the mean chain length of the polyoxymethylene glycols, which correlates to the mean molar mass of these, is critical in terms of solids precipitation in high-concentration aqueous formaldehyde solutions. That patent application, whose disclosure is hereby fully incorporated by reference into the present patent application, describes aqueous formaldehyde solutions comprising formaldehyde in the form of monomeric formaldehyde, methylene glycol and polyoxymethylene glycols in a total concentration x of ≧65% by weight, in which the mean molar mass $\overline{M}$ of the polyoxymethylene glycols as a function of the formaldehyde concentration is equal to or less than the values obtained according to the equation I.

$$\left(\frac{\overline{M}}{g/mol}\right) = 48 + 6.589 \cdot 10^{-1} \cdot \left(\frac{x}{\% \text{ by wt.}}\right) + 4.725 \cdot 10^{-2} \cdot \left(\frac{x}{\% \text{ by wt.}}\right)^2 - \quad (I)$$
$$3.434 \cdot 10^{-3} \cdot \left(\frac{x}{\% \text{ by wt.}}\right)^3 + 9.625 \cdot 10^{-5} \cdot \left(\frac{x}{\% \text{ by wt.}}\right)^4 -$$
$$1.172 \cdot 10^{-6} \cdot \left(\frac{x}{\% \text{ by wt.}}\right)^5 + 5.357 \cdot 10^{-9} \cdot \left(\frac{x}{\% \text{ by wt.}}\right)^6.$$

In this equation:

$\overline{M}$ mean molar mass x total concentration of formaldehyde in the form of monomeric formaldehyde, methylene glycol and polyoxymethylene glycols in % by weight (total formaldehyde concentration).

The aqueous formaldehyde solutions described preferably display no precipitation of solids over a period of at least one minute, preferably at least 5 minutes, particularly preferably at least one hour, at temperatures of generally from −5 to 180° C., preferably from 10 to 100° C., particularly preferably from room temperature to 50° C., i.e. at temperatures at which reactions with formaldehyde are usually carried out. In particular, no aging at elevated temperature is necessary. In fact, increasing the temperature is generally undesirable.

The aqueous formaldehyde solutions provided by the invention can thus be used wherever reactions with suitable compounds occur within the time frame specified.

The aqueous formaldehyde solutions described are prepared by removal of water or a water-containing mixture, preferably by rapid removal within a period of generally from 1 second to 5 hours, preferably from 5 seconds to 1 hour, particularly preferably from 10 seconds to 30 minutes.

The high-concentration formaldehyde solutions described are preferably prepared by at least partial evaporation of the aqueous formaldehyde solutions having a lower concentration, with thermal separation being carried out. This can be carried out in one or more stages, in cocurrent or in countercurrent.

Evaporation can be carried out using a helical tube evaporator or coiled tube evaporator, with the starting solution being fed under pressure to a preheater, being heated there and subsequently being depressurized to form vapor. This solution is then concentrated to the final product in the heated helical tube.

In the light of the above, it is an object of the present invention to further improve the process for concentrating an aqueous formaldehyde solution by evaporation of water in a helical tube evaporator.

This object is achieved by a process for preparing a high-concentration formaldehyde solution by removing water from a lower-concentration formaldehyde solution having a formaldehyde content of from 5 to 50% by weight, in which the lower-concentration formaldehyde solution is fed to a preheater and heated in the preheater, depressurized via a pressure maintenance device and concentrated in a helical tube evaporator to give a vapor stream and the high-concentration formaldehyde solution as bottom stream, wherein the heated lower-concentration formaldehyde solution is depressurized in the pressure maintenance device to give a two-phase mixture which is fed into the helical tube evaporator.

A decisive improvement in the process for concentrating the aqueous formaldehyde solution in the helical tube evaporator is thus achieved according to the invention by feeding the aqueous formaldehyde solution to be concentrated into this as a two-phase mixture.

The process of the present invention starts from a relatively low-concentration aqueous formaldehyde solution, i.e. an aqueous formaldehyde solution having a total formaldehyde content in the form of monomeric formaldehyde, methylene glycol and polyoxymethylene glycols of from 5 to 50% by weight.

This starting solution is firstly heated by means of a preheater. As preheaters, it is possible to use conventional types of apparatus such as shell-and-tube apparatuses, plate heat exchangers, spiral heat exchangers or electric heaters.

The pressure in the preheater is advantageously set by means of a downstream pressure maintenance valve so that the aqueous solution does not vaporize at any point in the preheater. The starting solution which has been heated in the preheater is subsequently depressurized in a pressure maintenance device to form a two-phase mixture, i.e. to form a gaseous phase and a liquid phase. This two-phase mixture is fed to the helical tube evaporator.

As a result of the mixture being fed in as a two-phase mixture, mixing of the phases occurs in the helical tube evaporator without moving parts being required for this purpose.

A further improvement in mixing can be achieved by appropriate design of the geometry, in particular the tube diameter of the helical tube evaporator, the total mass flow through the apparatus and the proportion of gas in the two-phase mixture, preferably so as to achieve a flow profile corresponding to a wavy film flow in the helical tube evaporator.

This results in intensive mixing of the liquid film, so that temperature and concentration gradients in the liquid film are effectively eliminated. Furthermore, high shear stresses prevail in the wall region, so that the cumulation of solids on the heated walls of the apparatus is effectively avoided. In general, gas velocities of from 20 m/s to several 100 m/s are set in the helical tube evaporator.

The evaporation rate to be achieved and thus the concentration of the formaldehyde in the final product is controlled by appropriate selection of the heating temperature of the apparatus.

A vapor stream is taken off from the helical tube evaporator and is fed to a downstream vapor separator to separate liquid and gas phases.

The gas phase can be completely or partially condensed in conventional condensers which are preferably operated as quench condensers, for example in upright shell-and-tube apparatuses. The condensates obtained, which comprise water together with formaldehyde and methylene glycols, can be concentrated further to about 50% by weight of formaldehyde in conventional evaporators.

The formaldehyde solutions obtained in this way can advantageously be recycled as feed stream to the helical tube evaporator unit, especially into the preheater.

The proportion of gas in the two-phase mixture which is fed to the helical tube evaporator can, for example, also be influenced by mixing a stripping gas, preferably nitrogen, into it upstream of the feed line to the helical tube evaporator.

The use of stabilizers to suppress precipitation of solids, which stabilizers could interfere in chemical reactions, is not necessary in the process of the invention. However, it is possible to add a stabilizer to the two-phase mixture before it is fed into the helical tube evaporator. The choice of stabilizer is not subject to any restrictions. The stabilizers can preferably be selected from among methanol, ethanol, propanols, butanols, urea and melamine. To further improve phase mixing in the helical tube evaporator, it is advantageous to provide devices suitable for this purpose, in particular valves, flow restrictors, ribs or knitted wire meshes.

Apart from operation in single pass, it is possible to recycle all or part of the bottom stream from the helical tube evaporator to the helical tube evaporator unit, i.e. into the preheater.

It is also possible to carry out the concentration of the aqueous formaldehyde solution in a plurality of stages by connecting two or more helical tube evaporator units in series, preferably with heat integration. Conventional apparatuses, i.e. apparatuses different from helical tube evaporators, in particular falling film evaporators, can also be used here, in particular in the first stage or stages of the concentration process.

The process of the invention thus has the advantage that the specific mode of operation of the helical tube evaporator enables very high surface-specific performances at short residence times to be achieved. For this mode of operation, it is, in particular, critical that the feed to the helical tube evaporator is a two-phase mixture, i.e. has a gas phase component and a liquid phase component. Furthermore, the mode of operation of the helical tube evaporator can be improved further by means of appropriate design of the geometry of the evaporator, in particular the diameter, by fixing the total mass flow to be passed through it and also the proportion of gas in the two-phase feed.

The short residence times resulting from the relatively high flow velocities set effectively prevents formation of higher polyoxymethylene glycols (corresponding to the fully established thermodynamic equilibrium), so that the solutions which have been concentrated remain homogeneous, i.e. without formation of solid phases, over comparatively long times.

Furthermore, the short residence times of the solution at relatively high temperatures effectively suppress the undesired formation of formic acid from formaldehyde.

The invention is illustrated below with the aid of an example:

EXAMPLE (FOR COMPARISON)

An aqueous solution containing 50% by weight of formaldehyde was fed at a flow rate of 10 kg/h into a falling film evaporator unit. The unit was equipped with an evaporator tube having dimensions of 25×2×3500 mm (external tube diameter×tube thickness×tube length) and having a heat transfer area of about 0.23 m². The pressure in the vapor space was set to 100 mbar, and the heating temperature to about 135° C.

A degree of evaporation of about 17% was achieved. This resulted in a total formaldehyde content in the bottom product of 60% by weight.

Even in the vapor space of the falling film evaporator, the solution displayed formation of solid oligomers of formaldehyde.

Attempts to operate the apparatus at higher degrees of evaporation led to rapid and irreversible coating of the heating surfaces.

EXAMPLE (ACCORDING TO THE INVENTION)

An aqueous solution having the same starting concentration as in the comparative example, i.e. 50% by weight of formaldehyde, was fed at a flow rate of 15 kg/h into a helical tube evaporator unit comprising, as most important equipment items, a preheater, a pressure maintenance valve and a helical tube evaporator. The helical tube evaporator was equipped with a glass helix having a length of 6 m, an internal diameter of 7 mm and a heat-transferring area of about 0.19 m².

The pressure at the outlet of the preheater was set to 1.7 bar, and the pressure at the outlet of the helical tube evaporator to 100 mbar.

The heating temperature in the preheater was 124° C., and that in the helical tube evaporator was 128° C.

The product exit temperature from the preheater was about 103° C., and that at the outlet of the helical tube evaporator was about 65° C. The proportion of gas on entry into the helical tube evaporator was 2%, based on the total stream. As a result of heating and the pressure drop along the helical tube evaporator, the proportion of gas rose to about 35% at the outlet of the helical tube evaporator.

A total formaldehyde content of about 75% by weight was established in the bottom product.

The solution which had been concentrated remain clear, i.e. without precipitation of solids, over a period of more than 2 hours.

Deposit formation in the helical tube evaporator unit was not observed.

The invention claimed is:

1. A process for preparing a high-concentration formaldehyde solution by removing water from a lower-concentration formaldehyde solution having a formaldehyde content of from 5 to 50% by weight, in which the lower-concentration formaldehyde solution is fed to a preheater and heated in the preheater, depressurized via a pressure maintenance device and concentrated in a helical tube evaporator to give a vapor stream and the high-concentration formaldehyde solution as bottom stream, wherein the heated lower-concentration formaldehyde solution is depressurized in the pressure maintenance device to give a two-phase mixture which is fed into the helical tube evaporator.

2. The process according to claim 1, wherein the high-concentration formaldehyde solution in the bottom stream of the helical tube evaporator contains at least 70% by weight of formaldehyde.

3. The process according to claim 1, wherein a stripping gas is mixed into the two-phase mixture before it is fed into the helical tube evaporator.

4. The process according to claim 1, wherein a stabilizer is introduced into the two-phase mixture before it is fed into the helical tube evaporator.

5. The process according to claim 1, wherein a wavy film flow is established in the helical tube evaporator by appropriate choice of the geometry of the evaporator and also of the operating conditions.

6. The process according to claim 1, wherein devices for achieving intensive mixing of the two-phase mixture are provided in the helical tube evaporator.

7. The process according to claim 1, wherein the vapor stream from the helical tube evaporator is partially or completely condensed in a condenser.

8. The process according to claim 7, wherein the condensed part of the vapor stream is recycled to the preheater.

9. The process according to claim 1, wherein all or part of the bottom stream from the helical tube evaporator is recycled to the preheater.

10. The process according to claim 2, wherein the high-concentration formaldehyde solution in the bottom stream of the helical tube evaporator contains at least 75% by weight of formaldehyde.

11. The process according to claim 3, wherein the stripping gas is nitrogen.

12. The process according to claim 4, wherein the stabilizer is methanol, ethanol, a propanol, a butanol, urea or melamine.

13. The process according to claim 5, wherein the operating conditions are the total mass flow and the gas content of the two-phase mixture which is passed through the helical tube evaporator.

14. The process according to claim 6, wherein the devices for achieving intensive mixing of the two-phase mixture are valves, flow restrictors, ribs or knitted wire meshes.

15. The process according to claim 7, wherein the condenser is a surface condenser.

16. The process according to claim 15, wherein the surface condenser is a quench condenser.

* * * * *